US008172765B2

(12) United States Patent  
Maksym et al.

(10) Patent No.: US 8,172,765 B2  
(45) Date of Patent: May 8, 2012

(54) METHOD OF ASSESSMENT OF AIRWAY VARIABILITY IN AIRWAY HYPERRESPONSIVENESS

(75) Inventors: Geoffrey N. Maksym, Dartmouth (CA); Carolyn A. Lall, Halifax (CA)

(73) Assignee: Dalhousie University, Halifax, Nova Scotia (CA)

( * ) Notice: Subject to any disclaimer, the term of this patent is extended or adjusted under 35 U.S.C. 154(b) by 1642 days.

(21) Appl. No.: 11/121,031

(22) Filed: May 4, 2005

(65) Prior Publication Data

US 2005/0247307 A1    Nov. 10, 2005

Related U.S. Application Data

(60) Provisional application No. 60/567,446, filed on May 4, 2004, provisional application No. 60/630,567, filed on Nov. 26, 2004.

(51) Int. Cl.  
*A61B 5/08* (2006.01)

(52) U.S. Cl. ........................................ 600/529; 600/538

(58) Field of Classification Search ........... 600/529–543  
See application file for complete search history.

(56) References Cited

U.S. PATENT DOCUMENTS

| | | | |
|---|---|---|---|
| 4,326,416 A | 4/1982 | Fredberg | |
| 5,984,872 A | 11/1999 | Vriend | |
| 6,015,388 A | 1/2000 | Sackner et al. | |
| 6,066,101 A | 5/2000 | Johnson et al. | |
| 6,074,350 A | 6/2000 | Macklem et al. | |
| 6,142,952 A | 11/2000 | Behbehani et al. | |
| 6,287,264 B1 | 9/2001 | Hoffman | |
| 6,383,142 B1 | 5/2002 | Gavriely | |
| 6,402,698 B1 | 6/2002 | Mault | |
| 6,440,083 B1 | 8/2002 | Fredberg | |
| 6,544,192 B2 | 4/2003 | Starr et al. | |
| 6,632,402 B2 | 10/2003 | Blazewicz et al. | |
| 6,662,032 B1 | 12/2003 | Gavish et al. | |

FOREIGN PATENT DOCUMENTS

| | | |
|---|---|---|
| CA | 2298547 | 4/1998 |
| CA | 2298553 | 4/1998 |
| CA | 2295525 | 3/1999 |

(Continued)

OTHER PUBLICATIONS

Randell et al. "Simple forced oscillatory technique and spirometry in assessment of bronchial responsiveness in non-asthmatic and asthmatic subjects", 1999 Blackwell Science Ltd, Clinical Psychology 19, 4, 321-328.*

(Continued)

*Primary Examiner* — Patricia Mallari  
*Assistant Examiner* — Christian Jang  
(74) *Attorney, Agent, or Firm* — Honigman Miller Schwartz and Cohn LLP; Fernando Alberdi; Jonathan P. O'Brien

(57) ABSTRACT

The invention relates to a method of assessing airway variability in airway responsiveness or asthma by measuring the variation of resistance (Rrs) by a forced oscillation technique utilizing either a single or a plurality of input frequencies during a plurality of respiratory cycles of a patient; calculating the statistical variability of the Rrs for the patient; and, correlating the statistical variability of the Rrs of the patient to a standard curve to quantify the degree of asthma of the patient. The invention also enables the effectiveness of a bronchoactive agent to be measured.

27 Claims, 17 Drawing Sheets

FOREIGN PATENT DOCUMENTS

| | | |
|---|---|---|
| CA | 2320063 | 8/1999 |
| CA | 2446445 | 11/2002 |
| GB | 2 055 046 A | 2/1981 |
| JP | 57-122846 | 7/1982 |
| WO | WO 00/33733 | 6/2000 |
| WO | WO 03/063703 A1 | 8/2003 |

OTHER PUBLICATIONS

Delacourt et al. "Use of the Forced Oscillation Technique to Assess Airway Obstruction and Reversibility in Children" Am J Respir Crit Care Med vol. 161. pp. 730-736, 2000.*

Ducharme, et al. "Pediatric Reference Values for Respiratory Resistance Measured by Forced Oscillation", Chest 1998; 113; 1322-1328, DOI 10.1378/chest.113.5.1322.*

Asthma Diagnosis Technology.

Variability analysis of oscillatory airway resistance in children; Hubert Trubel; Wolfgang K.R. Banikol; May 25, 2005.

Global Burden of Asthma; Matthew Masoli; Denise Fabian; Shaun Holt; Richard Beasley.

World Health Organization—Bronchial asthma; http://www.who.int/mediacentre/factsheets/fs206/en/print.html; Jul. 7, 2005.

Respiratory Mechanics in Infants: Physiologic Evaluation in Health and Disease; American Thoracic Society/European Respiratory Society; 1993.

Measurement of Low-Frequency Respiratory Independence in Infants; Peter D. Sly; Mark J. Hayden; Ferenc Petak; Zoltan Hantos; 1996.

Clinical Application of Forced Oscillation; Michael D. Goldman; Aug. 16, 2001.

Forced oscillation technique: from theory to clinical applications; D. Navajas; R. Farre; 2001.

Oscillation Mechanics of Lungs and Chest in Man; Arthur B. Dubois; Alfred W. Brody; David H. Lewis; B. Franklin Burgess, Jr.; Sep. 26, 1955.

Chest; FM Ducharme; GM Davis; GR Ducharme; Jul. 7, 2005.

Use of the Forced Oscillation Technique to Assess Airway Obstruction and Reversibility in Children; Delacourt; Lorino; Herve-Guillot; Reinert; Harf; Houssett; 2000.

Respiratory resistance by the forced oscillation technique in asthmatic children and cystic fibrosis patients; P. Lebecque; D. Stanescu; Nov. 29, 1996.

Chest; Mazurek; Marchal; Derelle; Hatahet; Moneret-Vautrin; Monin; Jul. 7, 2005.

Comparison of the Forced Oscillation Technique and the Interrupter Technique for Assessing Airway Obstruction and Its Reversibility in Children; Delacourt; Lorino; Fuhrman.

Chest; J. Hellinckx; K. De Boeck; M. Demedts; Jul. 7, 2005.

Total Respiratory Resistance and Reactance in Patients with Asthma, Chronic Bronchitis and Emphysema; Noord; Clement; Van De Woestijne; Demedts; Nov. 16, 1990.

Chest; Zerah; A.M. Lorino; H. Lorino; Harf; Macquin-Mavier; Jul. 7, 2005.

Forced oscillation total respiratory resistance and spontaneous breathing lung resistance in COPD patients; Farre; Peslin; Rotger; Barbera; Navajas; Feb. 15, 1999.

A New Look At the Pathophysiology of Asthma; Talmadge E. King, Jr., MD.

New Considerations About Measuring Airway Hyperresponsiveness; P.M. O'Byrne, M.B.; M.D. Inman, MD., Ph.D.; 2000.

Airway responsiveness to methacholine:effects of deep inhalations and airway inflamation; Brusasco; Crimi; Barisione; Spanevello; Rodarte; Pellegrino; 1999.

Homekinesis and short-term variability of human airway caliber; Que; Kenyon; Olivenstein; Macklem; Maksym; Mar. 20, 2001.

Changes of respiratory input impedance during breathing in humans; M. Cauberghs; K.P. Van De Woestijne; Jul. 13, 1992.

Effect of a previous deep inspiration on airway resistance in man; Jay A. Nadel; Donald F. Tierney; Jan. 13, 1961.

Airway Hyperresponsiveness in Asthma: A Problem of Limited Smooth Muscle Relaxation with Inspiration; Gwen Skloot; Solbert Permutt; Aklis Togias; Jul. 24, 1995.

Potent bronchoprotective effect of deep inspiration and its absence in asthma; Kapsali; Permutt; Laube; Scichilone; Togias; Feb. 21, 2000.

Cheng-Li Que, et al., "Homeokinesis and Short-term Variability of Human Airway Caliber", J. Appl. Physiol., Sep. 2001, pp. 1131-1141, vol. 91.

Sekizawa, K. et al., "Noninvasive method for detecting laryngeal narrowing with low-frequencey sound", J. Appl. Physiol.: Respirat. Environ. Exercise Physiol., 1983, pp. 591-597, vol. 55, No. 2.

Schweitzer C. et. al., "Respiratory impedance response to a deep inhalation in asthmatic children with spontaneous airway obstruction", Eur Respir J, 2002, vol. 19, pp. 1020-1025.

Schuessler T. F., et al., "A computer-controlled research ventilator for small animals: design and evaluation", 1995, vol. 42, No. 9, pp. 860-866.

Macleod, et al., "Respiratory Input Impedance Measurement: Forced Oscillation Methods", Med & Biol Eng & Computing, 2001, vol. 39, pp. 505-516.

* cited by examiner

METHOD OF ASSESSMENT OF AIRWAY VARIABILITY IN AIRWAY HYPERRESPONSIVENESS The present application claims the benefit of U.S. Provisional Patent Application No. 60/567,446, filed on May 4, 2004, and of U.S. Provisional Patent Application No. 60/630,567, filed on Nov. 26, 2004, the entire teachings of which are incorporated herein by reference.

FIELD OF THE INVENTION

The invention relates to a method of assessing airway variability in airway responsiveness or asthma by measuring the variation of resistance (Rrs) by a forced oscillation technique utilizing either a single or a plurality of input frequencies during a plurality of respiratory cycles of a patient; calculating the statistical variability of the Rrs for the patient; and, correlating the statistical variability of the Rrs of the patient to a standard curve to quantify the degree of asthma of the patient. The invention also enables the effectiveness of a bronchoactive agent to be measured.

BACKGROUND OF THE INVENTION

Asthma is a disease affecting 100-150 million people worldwide with deaths from asthma reaching 180 000 annually [i]. Asthma affects all age groups but often starts in childhood and is the most common chronic childhood disease affecting 6.3 million children worldwide [ii]. Asthma is also more prevalent in the developing world with the incidence in children increasing by approximately 75% every 10 years in the United States [iii]. However currently there is no easy accepted non-invasive method of measuring pulmonary function in children under the age of 6.

The standard measure of lung function used in older children and adults is spirometry, a learned manoeuvre that depends on the active cooperation of the subject, therefore it does not produce reliable and reproducible results in young children (<6 yr). Techniques used in infants are not suitable over the age of one year, and usually require sedation [iv,v]. The forced oscillation technique offers a non invasive method of assessing lung mechanics that requires only passive patient cooperation [vi,vii]. FOT can also be applied in adults, and is also useful when spirometry is difficult, unpractical or infeasible, for example in the assessment of the elderly, paralysed and unconscious as well as in sleep studies and with mechanically ventilated patients.

The forced oscillation technique was first introduced in 1956 by Dubois and colleagues [viii] as a method of characterizing respiratory mechanics. In this technique, low-amplitude pressure oscillations are applied at the patient's airway opening during spontaneous breathing, the mechanical properties of the patient's respiratory system are derived from the pressure and flow signals recorded at the airway opening. Respiratory system impedance (Zrs) is a ratio of the Fourier transforms of pressure and flow, where the real and imaginary parts of Zrs are the resistance (Rrs) and reactance (Xrs) of the respiratory system. These mechanical properties of the respiratory system are indicative of airway obstruction. FOT has been shown to provide reproducible Rrs values at fixed frequencies as a function of sex, age and height in children [ix]. Mean Rrs has been found to provide reproducible and reliable results in healthy children, asthmatic children and children with cystic fibrosis. These results are concordant with forced expiratory volume in 1 second ($FEV_1$) measures in the children who were able to perform FEV1 [x,xi,xii,xiii,xiv].

FOT studies in adults have shown that mean Rrs and mean respiratory system reactance (Xrs) provide an indicator of airway caliber and can distinguish between asthma, chronic bronchitis and emphysema [xv,xvi,xvii].

Airway hype rresponsiveness is the exaggerated airway narrowing which occurs in response to airway challenge with a wide variety of pharmacological agonists and non-specific irritants such as cold, dry air and oxidant gases [xviii]. One standard measurement of airway hyperresponsiveness is performed by delivering methacholine or histamine to inhibit deep inhalations and increase airway hyperresponsiveness in increasing doses and measuring $FEV_1$ after each dose. Asthma is indicated by a smaller concentration that elicits a measured decrease in $FEV_1$ indicating a greater reactivity of the airways [xix,xx]. More recently, increased variation in airway resistance, standard deviation of Rrs measured by FOT in adults, has been shown to be a useful measure of airway smooth muscle reactivity and thus bronchial hyperresponsiveness [xxi]. Airflow limitation in bronchial hyperresponsiveness is largely determined by airway smooth muscle constriction. Airway diameters have been shown to be constantly changing within a breathing cycle and over short periods of time [xxii]. This leads to a respiratory system resistance that also varies over a breathing cycle, which can be reduced by deep inhalation [xxiii]. Lack of significant bronchodilation or bronchoprotection due to deep inhalation may contribute to the variability in airway calibre that characterizes asthma [xxiv,xxv].

SUMMARY OF THE INVENTION

In accordance with the invention, there is provided a method of assessment of airway variability in airway responsiveness or asthma comprising the steps of measuring the variation of resistance (Rrs) by a forced oscillation technique utilizing either a single or a plurality of input frequencies during a plurality of respiratory cycles of a patient; calculating the statistical variability of the Rrs for the patient; and, correlating the statistical variability of the Rrs of the patient to a standard curve to quantify the degree of airway responsiveness or asthma of the patient.

In accordance with an alternate embodiment, the invention also provides a method of determining the effectiveness of a pharmacological agonist or antagonist comprising the steps of:
  measuring the variation of resistance (Rrs) by a forced oscillation technique utilizing either a single or a plurality of input frequencies during a plurality of respiratory cycles of a patient;
  measuring the variation of resistance (Rrs) by a forced oscillation technique utilizing a plurality of input frequencies during a plurality of respiratory cycles of a patient having been administered pharmacological agonist or antagonist;
  calculating the statistical variability of the Rrs for the patient for each of the first two steps; and,
  comparing the statistical variability of the Rrs to determine the effectiveness of the pharmacological agonist or antagonist.

In accordance with another embodiment, the invention provides a method of determining the effectiveness of a pharmacological agonist or antagonist on altering airway diameter variability comprising the steps of:
  measuring the variation of reactance (Xrs) by a forced oscillation technique utilizing a plurality of input frequencies during a plurality of respiratory cycles of a patient both pre- and post-administration of a pharmacological agonist or antagonist;

calculating the Xrs for the patient for each of the pre- and post-administration steps; and, comparing Xrs to determine the effectiveness of the pharmacological agonist or antagonist.

A method for determining baseline values of variations of resistance (Rrs), variations in reactance (Xrs) and standard deviation of resistance (SDRrs) and the changes in these values in response to bronchoactive agents comprising the steps of:

measuring and storing closed impedance (Zc);

measuring and storing open impedance (Zo)

measuring and compensating baseline subject impedance Zm(t) over several cycles to determine Zrs(t);

measuring and comparing Rrs, Xrs and variations in Rrs and Xrs;

administering a broncho active agent to a patient;

measuring post drug impedance $Zm_p$ and compensating to determine $Zrs_p$;

calculating post-drug and pre-drug Rrs, Xrs and variation in Rrs and Xrs;

comparing post-drug and pre-drug values of Rrs, Xrs and variations in Rrs and Xrs to standard values to determine if the Rrs, Xrs and variation in Xrs and Rrs are normal or abnormal.

BRIEF DESCRIPTION OF THE DRAWINGS

The invention is described with reference to the following drawings wherein.

DETAILED DESCRIPTION OF THE INVENTION

In accordance with the invention, a patient study was performed in order to measure the statistical variation in the respiratory system resistance (Rrs) by a forced oscillation technique (FOT). The study provided a measure of baseline bronchial activity and thus airway smooth muscle activity in terms of optimal frequency of measurement, sensitivity in distinguishing between asthmatic and control children and a measure of bronchodilator (BD) effect in asthmatics which also enabled distinguishing between asthmatic and control children. The study also measured the reactance of the patient to determine changes in airway stiffness and degree of airway closure caused by changes in airway smooth muscle activity, in terms of optimal frequency of measurement, sensitivity in distinguishing between asthmatic and control children and a measure of bronchodilator (BD) effect in asthmatics, which also enabled distinguishing between asthmatic and control children.

EXPERIMENTAL

The study measured, by FOT, the median Rrs, standard deviation of Rrs (SDRrs) and Xrs at several frequencies between 4 and 34 Hz of a) asthmatic children and b) non-asthmatic children using spirometry performed both pre- and post-bronchodilator.

Hypothesis: Children with asthma have a greater value of both median Rrs and standard deviation of Rrs compared to control children and both may be negatively correlated with $FEV_1$ measurements. Bronchodilator administration reduces median Rrs and standard deviation of Rrs. Bronchodilator administration increases Xrs.

Figure 1:
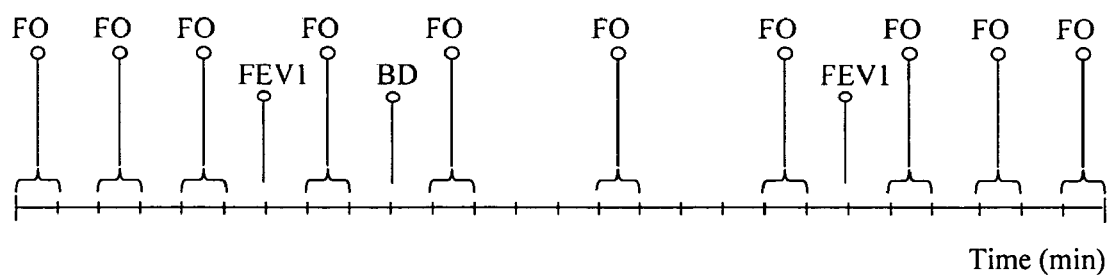
FIG. 1 is a schematic diagram of a test protocol, where FO is a forced oscillation measurement, and BD is administration of a pharmacological agonist or antagonist.

Protocol: Forty four physician-diagnosed asthmatic children between the ages of 7 and 13 were measured. The test protocol followed for each child is shown in FIG. 1.

Approximately thirty control children in the same age group with no history of respiratory problems were also measured. Half of the control children were given a placebo instead of a bronchodilator.

Flow-volume curves were recorded with a portable, pneumotachograph-based spirometer (PrestoFlash, Burdick, Inc., Milton, Wis.) to determine $FEV_1$ and $FEF_{25-75}\%$. This spirometer was calibrated daily with a volumetric syringe. Acceptance of flow volume curves was according to international criteria "Standardization of Spirometry, 1994 Update. American Thoracic Society. *Am J Respir Crit Care Med* 152: 1107-1136, 1995." Percent predicted values were calculated based on reference values for this age group "Knudson, et al. The maximal expiratory flow-volume curve. Normal standards, variability, and effects of age. *Am Rev. Respir Dis.* 113:587-600, 1976.

Each forced oscillation (FO) measurement was made using a custom FOT device constructed at Dalhousie University. The FOT device included pressure and flow transducers upon a breathing tube and a system for generating low-amplitude pressure oscillations (approximately ±1 cm $H_2O$) at multiple frequencies ranging from 4-34 Hz. The signal driving the pressure oscillations was composed of frequency components at 4, 6, 10, 14, 22, 26 and 34 Hz within a one second oscillation period that was continuously repeated. While different oscillation period durations could be chosen depending on the oscillation frequencies, as long as the oscillation period was an integer multiple of the inverse of all oscillation frequencies, one second was used in all cases. Each patient was asked to breathe through the breathing tube for three recording periods of one minute duration with nose clips on and with their cheeks supported. Between each of the one minute recording periods were provided breaks of approximately 10 seconds during which patients could swallow if needed. Pressure and flow data were collected at 700 Hz using a data acquisition system. For each second of the FO measurement median Rrs, standard deviation of Rrs, median Xrs and standard deviation of Xrs were measured at 4, 6, 10, 14, 22, 26 and 34 Hz. A bias fan provided approximately 12 L/min of fresh air through long stiff walled flexible tubes and the subject breathed through a mouthpiece and filter.

The impedance of the patient's respiratory system (Zrs) is derived from pressure and flow signals according to the formulae:

$$Zm = \frac{P(f)}{\dot{V}(f)} \quad (1)$$

$$Zrs = \frac{ZcZm}{Zc - Zm} - \frac{ZoZc}{Zo + Zc} \quad (2)$$

where P(f) and V(f) are the Fourier transforms of pressure and flow respectively of one or more oscillation periods; Zc and Zo are calibrated impedances obtained with the FOT device system closed (Zc) and open to the atmosphere (Zo), Zm is a time series of the measured impedance. Equation (1) and (2) are applied for each repeated oscillation period, forming a time series of Zm and Zrs with lengths equal to the number of oscillation periods. If multiple oscillation periods of pressure and flow are used in the Fourier transforms of Equation (1), the length of Zm and Zrs correspondingly decreases by that multiple. Zc and Zo are typically calculated from recordings of up to 1 minute or until coherences>0.95 are achieved. The correction of Zm by the system impedances compensates for resistive and reactive losses within the measuring device and any filter at the patient attachment as described in "Schuessler T F and Bates J H. A computer-controlled research ventilator for small animals: design and evaluation. *IEEE Trans Biomed Eng* 42: 860-866, 1995."

Successful application of the method required that measurement of Zrs be calculated including compensation for the impedance of the device (including any tubing or filters between the device and the patient). The impedance of the device is a significant amount of the measured Zrs and should be removed from Zm to accurately determine Zrs. This was performed by providing an oscillatory pressure signal producing an oscillatory flow signal (consisting of either a single frequency or a range of frequencies as described above), and recording a measurement of impedance (Zm) with no patient at the device opening (ie. the open impedance or Zo), and another measurement of impedance but with the patient attachment closed by a stopper so that there are no leaks (ie. the closed impedance or Zc). After obtaining Zo and Zc with good coherence (>0.95) patient Zrs and thus Rrs and Xrs can then be accurately calculated from Equations 1 and 2 above, when the Zm is recorded from a patient. Zrs is thus calculated from Zm, Zc and Zo forming a time series usually up to 180 points in length calculated once per oscillation period (1 second) from the three concatenated one minute recording periods, and cycles with inadequate coherence or signal to noise ratio are removed.

Figure 2:
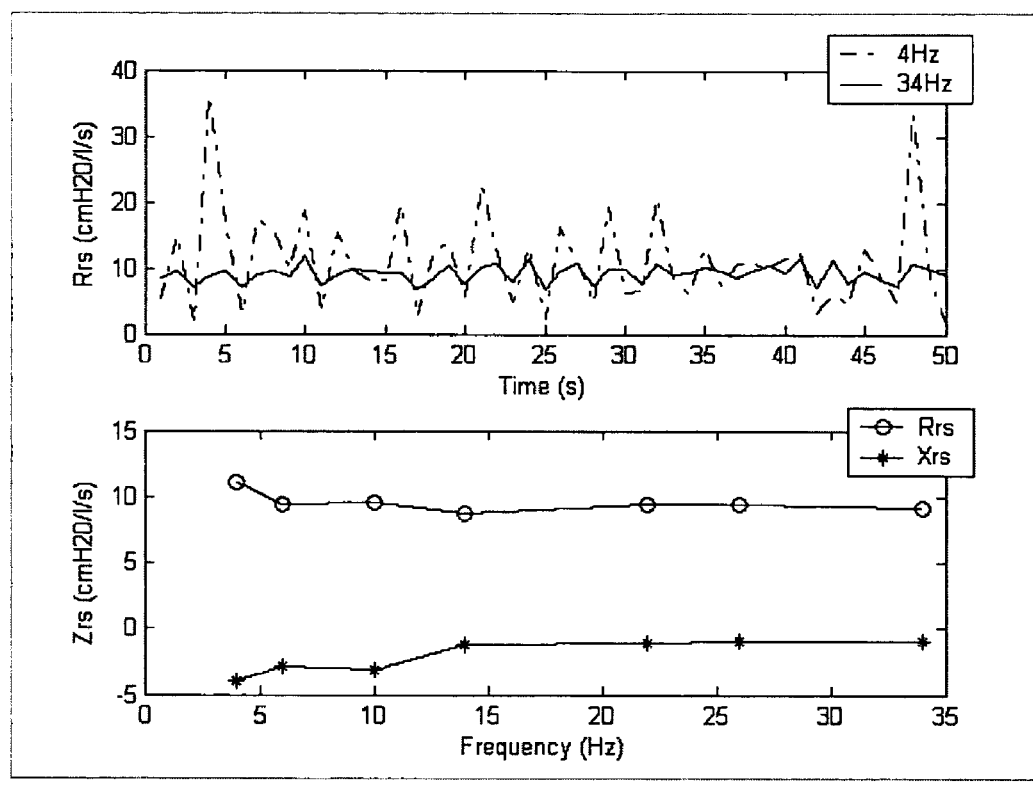
FIG. 2 are two plots with the top panel showing FOT Rrs over time calculated once per second at 4 and 34 Hz in an asthmatic child and the bottom panel showing FOT median Rrs and median Xrs over frequency in an asthmatic child calculated from 180 seconds.

Rrs and Xrs (FIG. 2) are the real and imaginary parts of Zrs respectively. Rrs, Xrs and variation in Rrs were analyzed at different frequencies in asthmatic children and control children before and after a BD performed both pre- and post-spirometry.

This allowed median Rrs, variation in Rrs and median Xrs calculated from the time series of Zrs to be examined over the frequency range 4-34 Hz, the effect of a BD on mechanical properties of the respiratory system of asthmatic and non-asthmatic children to be evaluated, the difference in mechanical properties of the respiratory system in control and asthmatic patients to be determined and the effectiveness and sensitivity of spirometry, median FOT Rrs, standard deviation of FOT Rrs, and median FOT Xrs to be evaluated.

Results:

Asthmatics (Table 1) were physician diagnosed and most were taking regular anti-inflammatory medication.

TABLE 1

| Summary of asthmatic patient population | |
| --- | --- |
| Male/Female | 25/15 |
| Age (yrs) | 8-12 |
| Height (cm) | 124-158 |
| Weight (kg) | 21-77 |

Figure 3:
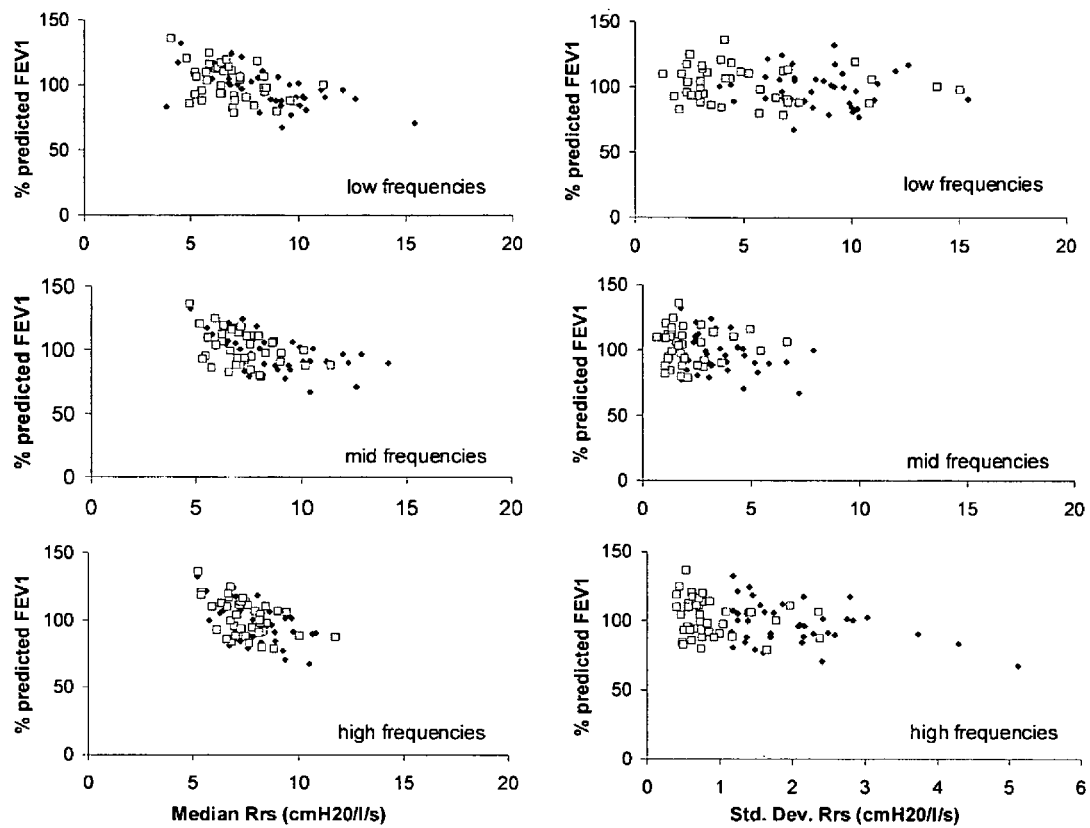
FIG. 3 are plots showing percent predicted FEV1 vs. median Rrs and FEV1 vs. standard deviation of Rrs from asthmatic children at low, middle and high frequencies before (diamonds) and after (squares) bronchodilator, with one diamond and one square from each subject.

In the asthmatic cohort median Rrs was negatively correlated with $FEV_1$, with correlation coefficients of 0.561, 0.546 and 0.563 at low, middle and high frequency oscillations where low frequency includes average measurements at 4 and 6 Hz, middle frequency includes average of 10 and 14 Hz and high frequency includes average of 22, 26 and 34 Hz (FIG. 3, left panels, diamonds).

Figure 4:
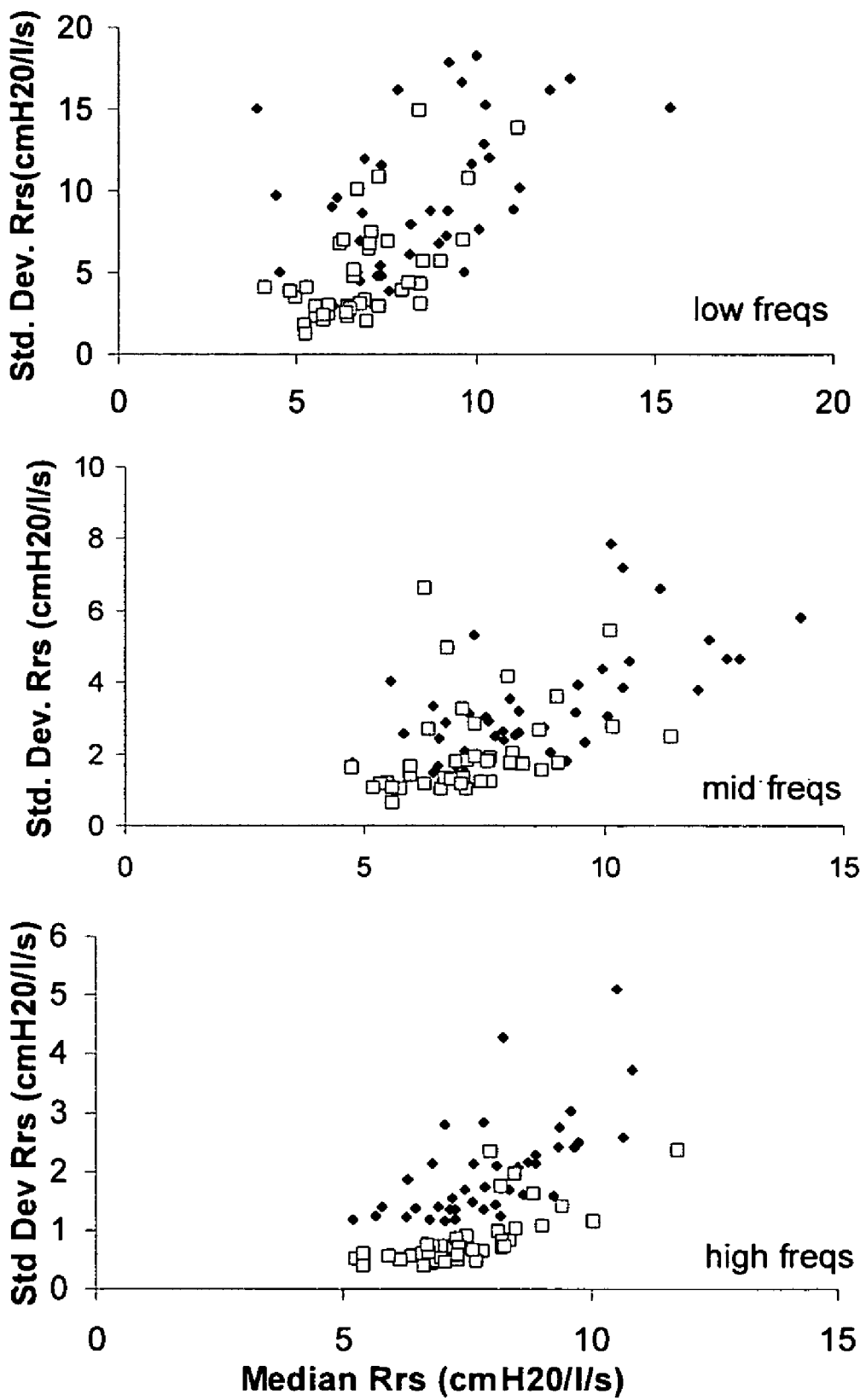
FIG. 4 are three plots of standard deviation of Rrs vs. median Rrs at low, middle and high frequencies pre (diamonds) and post (squares) bronchodilator from each asthmatic child.

Thirty eight of the forty children did not show clinically significant changes in $FEV_1$ or Rrs values after bronchodilator administration (p>0.05). This is most likely because most were taking regular anti-inflammatory medication. Median increase in $FEV_1$ was 3.5±0.7% and decrease in Rrs was 16.9±2.8%, 14.2±2.1% and 5.4±1.3% at low, middle and high frequencies seen as a slight upward and leftward shift from baseline to post bronchodilator values in the left pane is of FIG. 3 and in FIG. 4 where diamonds are baseline values from each subject and squares are post-bronchodilator values from each subject. However, standard deviation of Rrs significantly decreased after bronchodilator administration by 40.1±5.8%, 36.0±6.5% and 56.2±2.1% (p<0.05) at low, middle and high frequencies seen as a slight upward and large leftward shift from baseline (diamonds) to post-bronchodilator values (squares) in the right panels of FIG. 3 and downward shift from baseline (diamonds) to post-bronchodilator values (squares) in FIG. 4.

Figure 5:
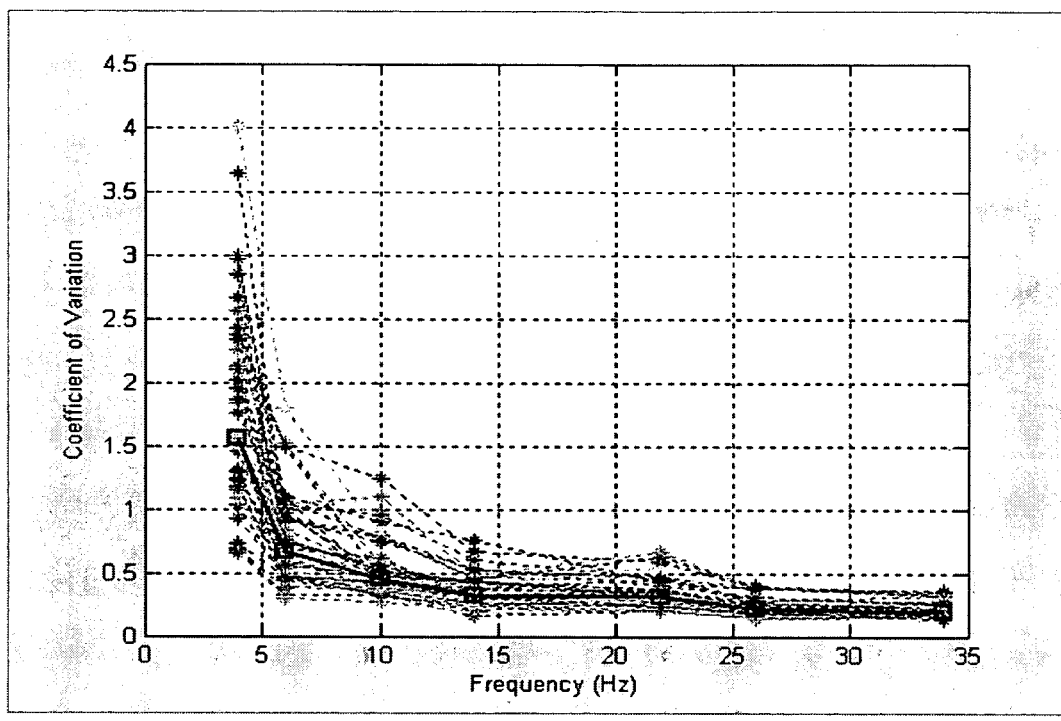
FIG. 5 is a plot of the coefficient of variation of Rrs vs. frequency in all asthmatic subjects where each line is from a different subject.

The coefficient of variation of Rrs measurements decreased as the frequency increased. This may be due to contamination of the signals by low frequency noise introduced by breathing (FIG. 5).

Figure 6:
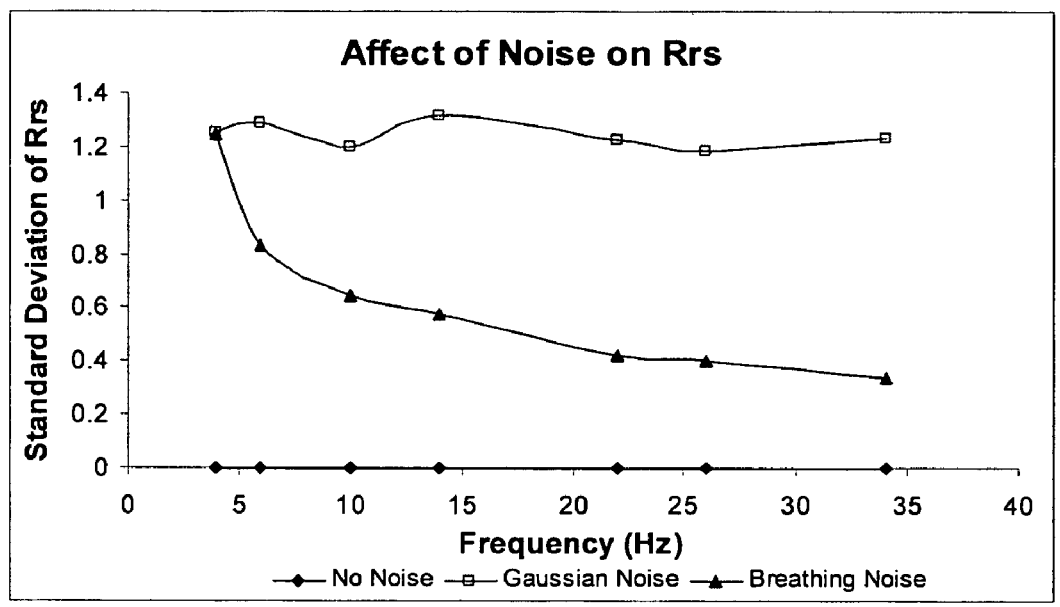
FIG. 6 is a plot of the simulated effect of noise on Rrs values.

A simulated system was created to determine the effects of adding different types of noise to the measurements. Adding Gaussian noise increased the standard deviation of Rrs by a constant (FIG. 6). However, adding noise similar to the type of noise introduced by breathing during measurements, that follows a 1/frequency curve, caused the calculated Rrs values to have higher standard deviation at low frequencies (FIG. 6). This was similar to the pattern of standard deviation of Rrs seen in the actual measurements (FIG. 5). This indicates that measurements below 20 Hz are more likely to be affected by breathing and may be less reliable than those measured at higher frequencies.

In conclusion, bronchodilator administration only slightly decreased median resistance and $FEV_1$ in asthma but significantly reduced variability in airway resistance. Thus, measurement of Rrs by FOT at frequencies not affected by breathing noise (typically above 10 Hz) may provide a useful measure of airway smooth muscle activity by measuring variations in Rrs not detected by traditional lung function measurements such as spirometry in children with asthma. This would also be useful in adults as it does not require a learned manoeuvre.

Figure 14:
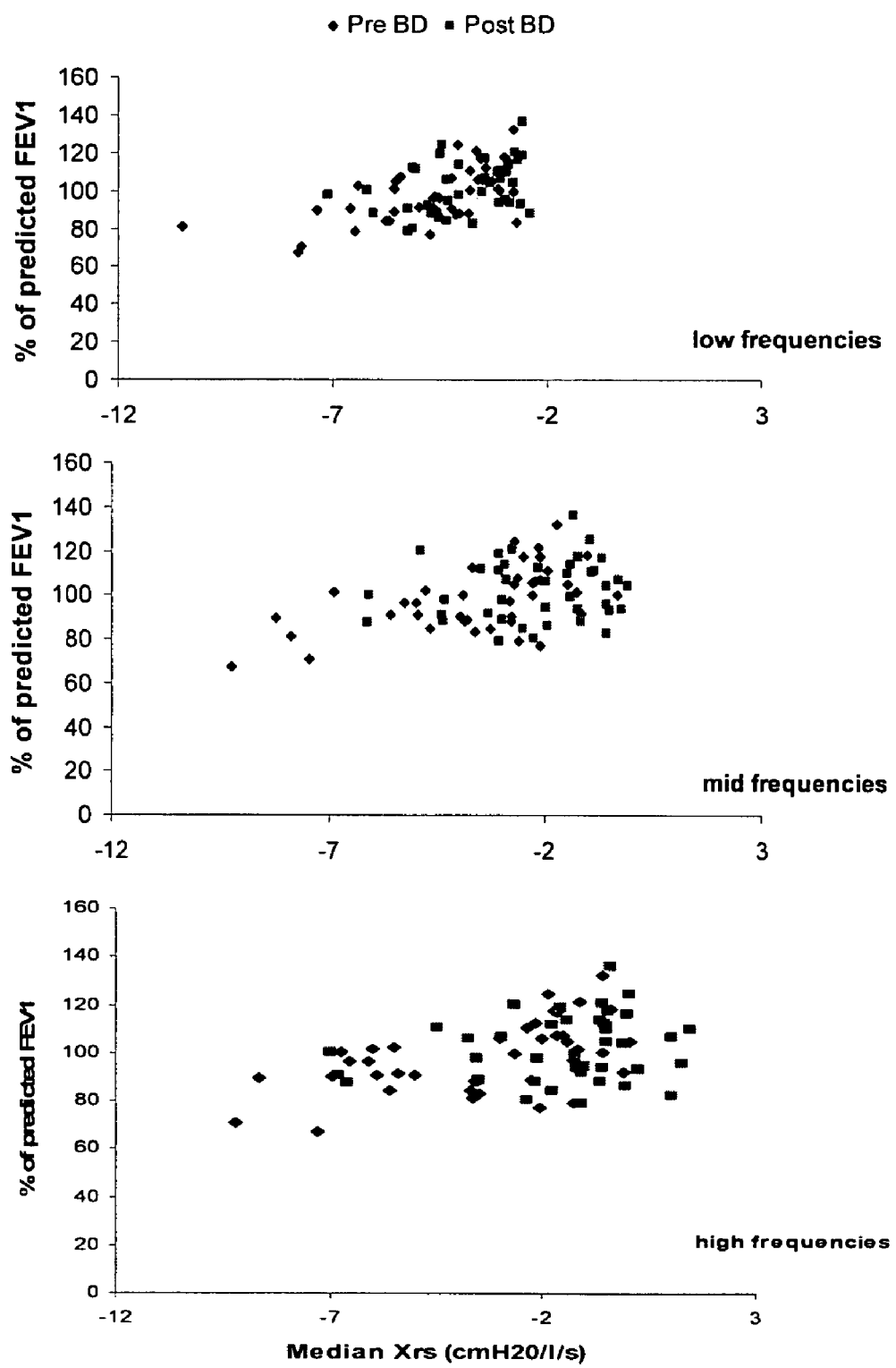
FIG. 14 is a plot of percent predicted FEV1 versus median Xrs from children with asthma pre (diamonds) and post bronchodilator (squares) at low, mid and high frequencies.

In addition, it was also found that Xrs, particularly measured at higher frequencies is a sensitive measure of bronchodilator effect as shown in FIGS. 14-18. More specifically, FIG. 14 shows the percent predicted FEV1 versus median Xrs from children pre- (diamonds) and post-bronchodilator (squares) at low, mid and high frequencies.

Figure 15:
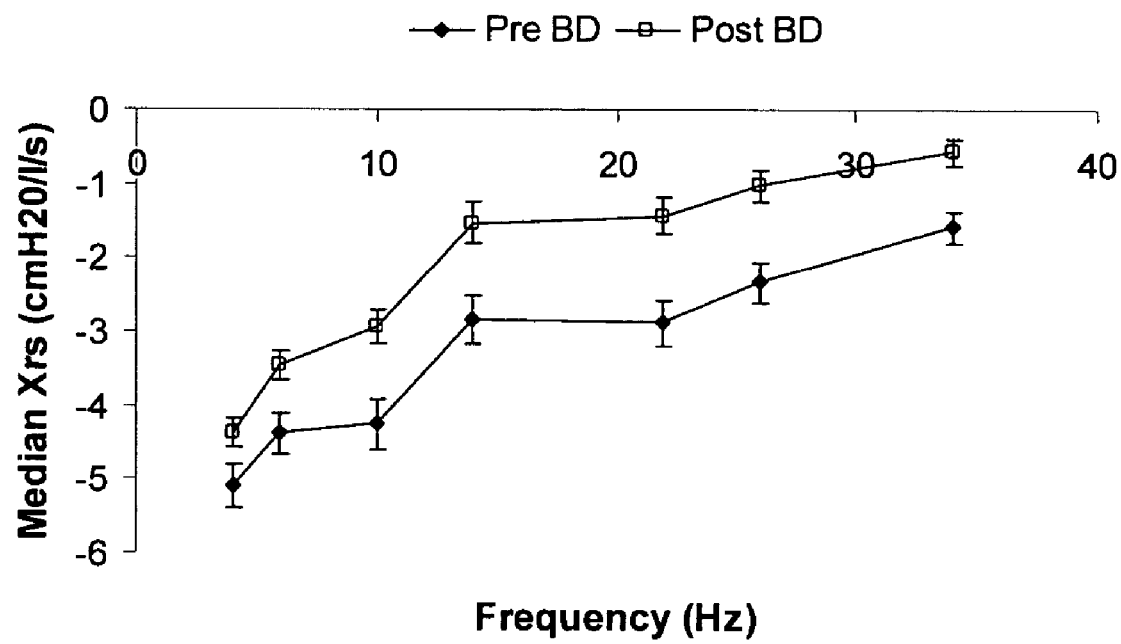
FIG. 15 is a plot of median Xrs pre- and post-bronchodilator in asthmatic children versus frequency.

FIG. 15 shows median reactance pre- and post-bronchodilator in asthmatic children versus frequency.

Figure 16:
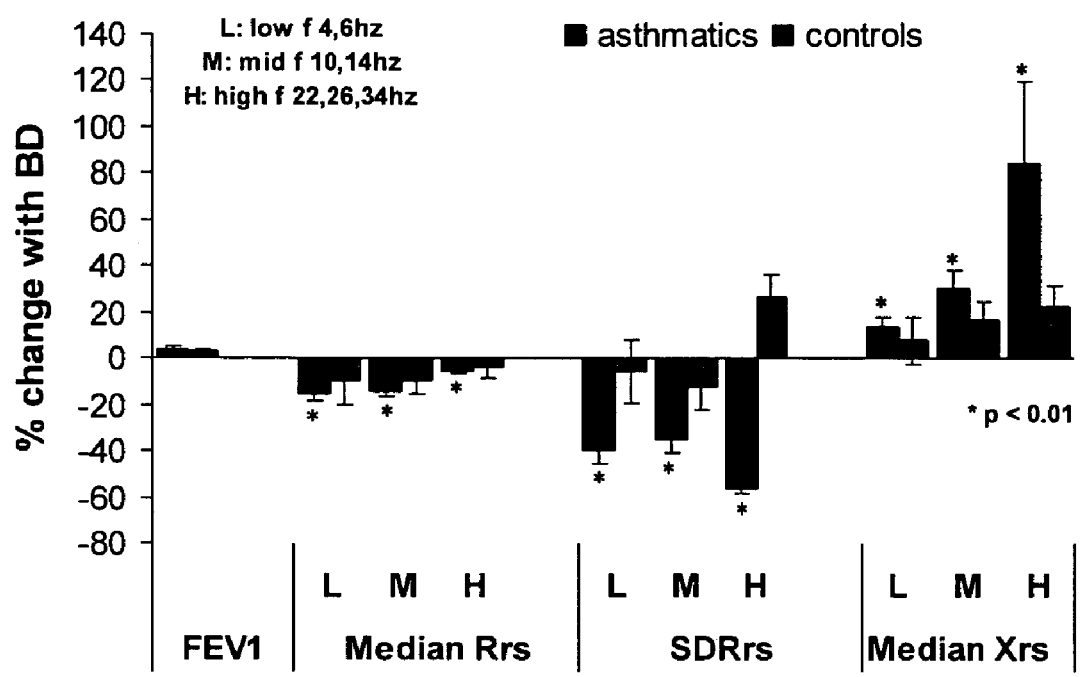
FIG. 16 is a plot showing a comparison of FEV1%, median Rrs, SDRrs and median Xrs in response to BD, with error bars showing standard error.

FIG. 16 is a comparison of FEV1%, median Rrs, standard deviation of resistance (SDRrs) and median Xrs in response to BD. This shows that SDRrs and median Xrs are more sensitive measures of bronchodilator effect than either FEV1 or Median Rrs, in children with asthma aged 6-9.

Figure 17:
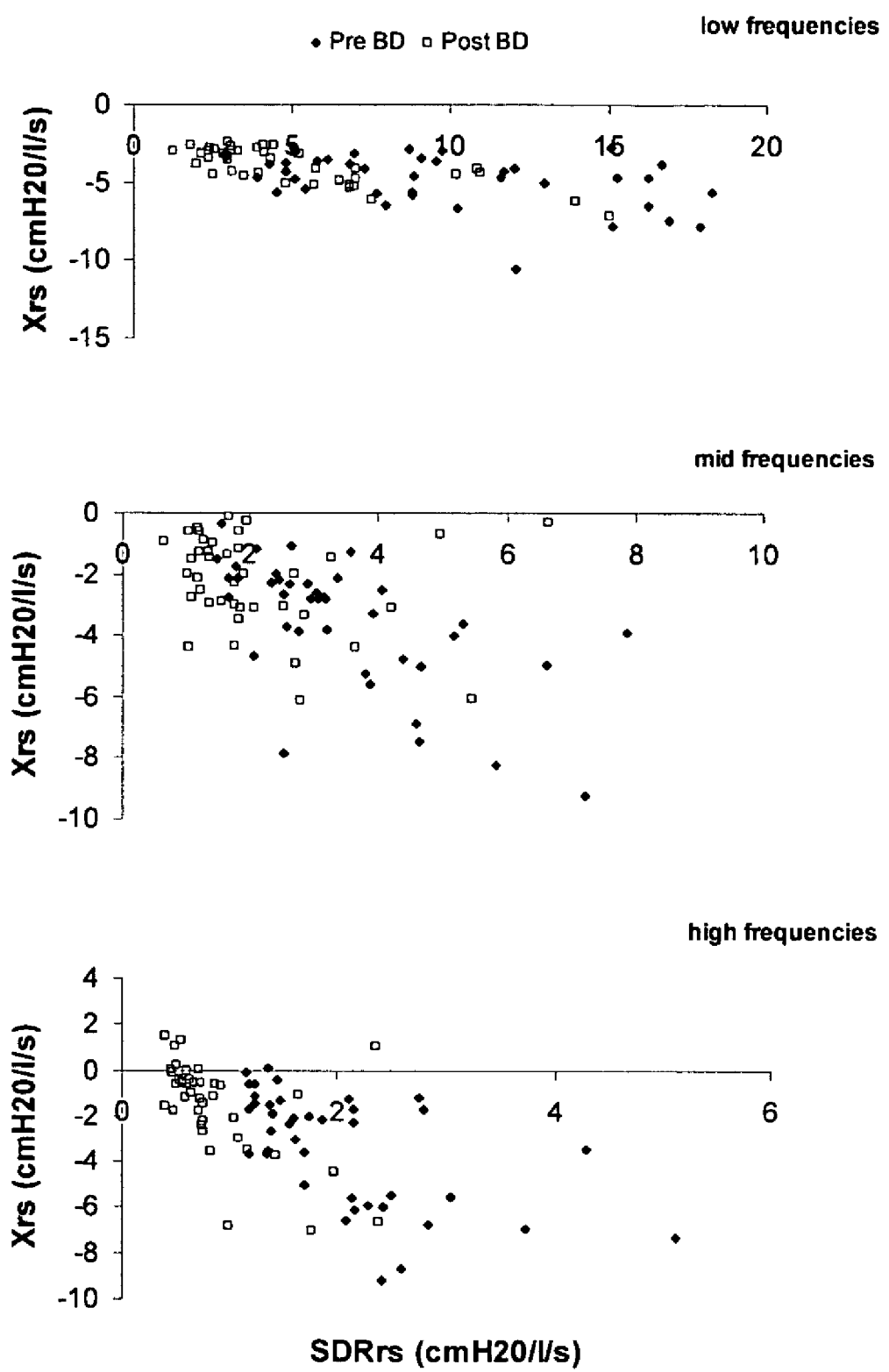
FIG. 17 is a plot of the relationship between SDRrs and Xrs before bronchodilator (diamonds) and post bronchodilator (squares) in children with asthma.

FIG. 17 shows the relationship between SDRrs and Xrs before bronchodilator (diamonds) and post bronchodilator (squares) in children with asthma. Each point represents the Xrs and SD Rrs from an individual and shows there is a moderate dependency between Xrs and SDRrs either before or after bronchodilator, such that those with high SDRrs also have low Xrs. Thus, measures of Xrs and SDRrs can be used in combination for diagnosing and monitoring asthma.

Figure 18:
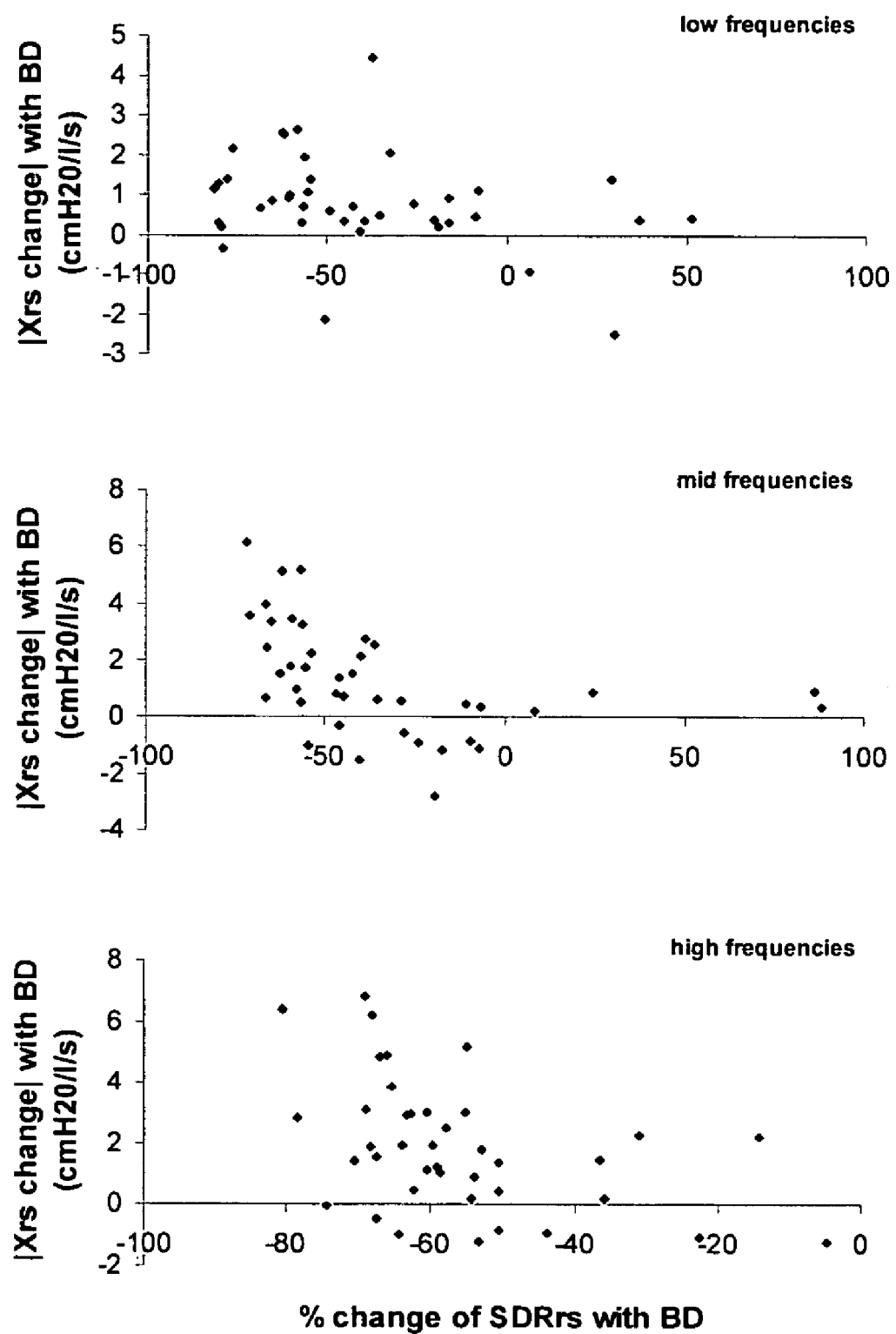
FIG. 18 is a plot of the relationship between % change in SDRrs with bronchodilator and change in Xrs with bronchodilator in children with asthma.

FIG. 18 shows the relationship between % change in SDRrs with bronchodilator and change in Xrs with bronchodilator in children with asthma. Each point represents the Xrs and SDRrs from an individual. It is apparent that a decrease in SDRrs is usually found with an increase in Xrs (especially at mid frequencies). Thus these measures could be used together to determine the efficacy of a particular bronchodilator.

Control Data with Placebo

The control data with half taking a placebo instead of a bronchodilator was collected.

The control data with half taking a bronchodilator was collected.

The controls (Table 2) were all children with no history of respiratory illness.

TABLE 2

Summary of the control patient population

| Male/Female | 8/7 |
| --- | --- |
| Age (yrs) | 7-13 |
| Height (cm) | 124-163 |
| Weight (kg) | 28-65 |

Median Rrs was negatively correlated with $FEV_1$, with correlation coefficients of 0.531, 0.555, and 0.436 at low, middle and high frequency oscillations.

There was not a significant change in $FEV_1$ with placebo administration with an average increase of 1.3±0.13% increase. There also was no significant change in median Rrs and standard deviation of Rrs with placebo administration.

Figure 7:
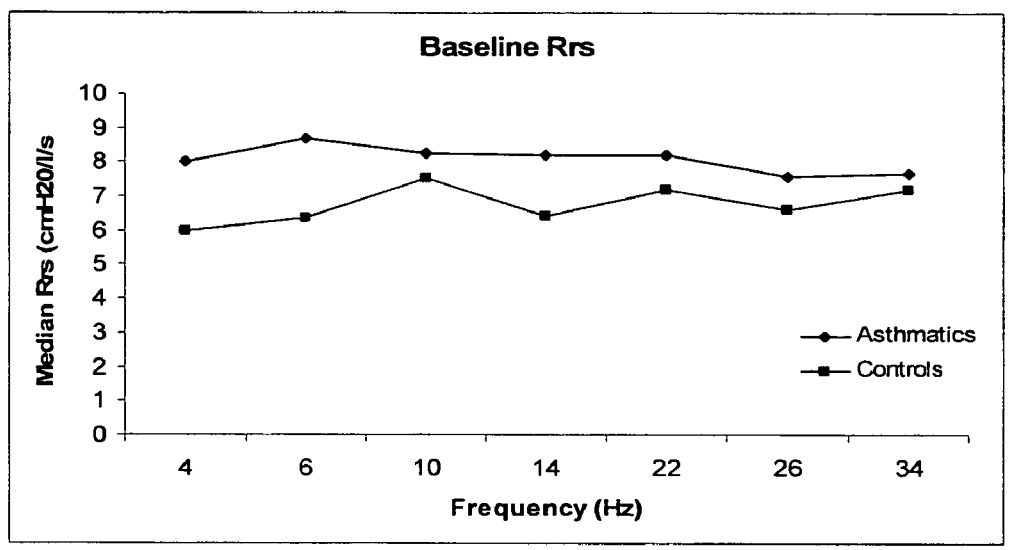
FIG. 7 is a plot of median Rrs in asthmatic and control children.

There was not a significant difference (7.62%, p>0.05) in baseline $FEV_1$ measured in controls and asthmatic children. Median resistance of asthmatics was significantly (p<0.05) higher than controls at frequencies equal to or lower than 26 Hz with a percent difference of 28.9% and 31.1% at 4 and 6 Hz respectively (FIG. 7). This shows that Median Rrs measured at 4 or 6 Hz is approximately 4 times more sensitive than $FEV_1$ as an indicator of asthma in children.

Figure 8:
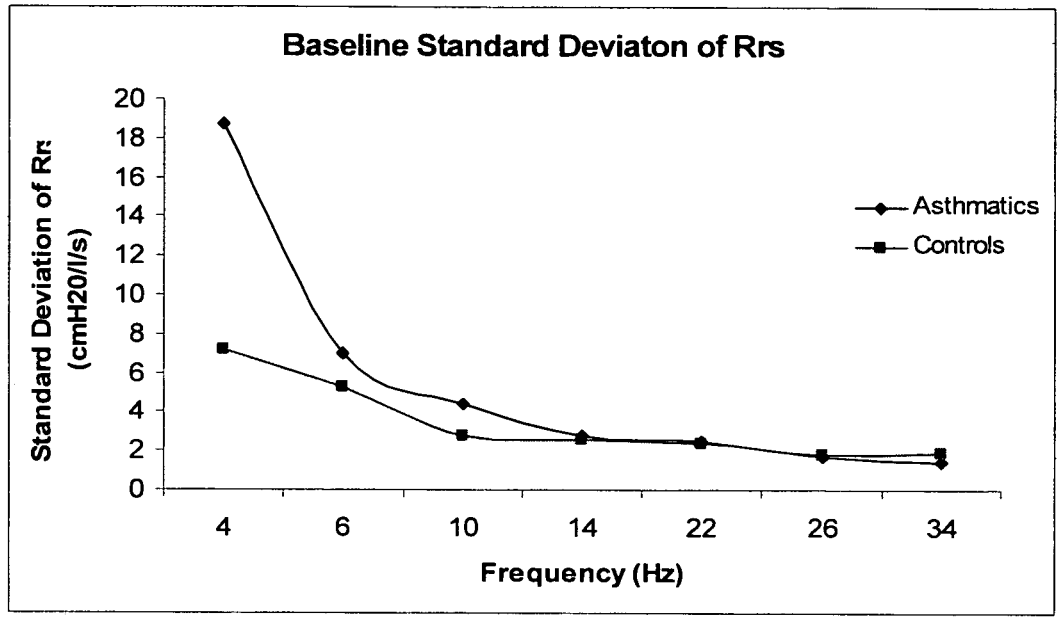
FIG. 8 is a plot of the baseline standard deviation of Rrs in asthmatic and control children.

Standard deviation of Rrs was 88.65% higher in asthmatics compared to controls at 4 Hz but not significantly different (p>0.05) at the other frequencies measured (FIG. 8). Since we believe low frequency measurements were contaminated by noise this may indicate that noise was greater in the asthmatics.

Figure 9:
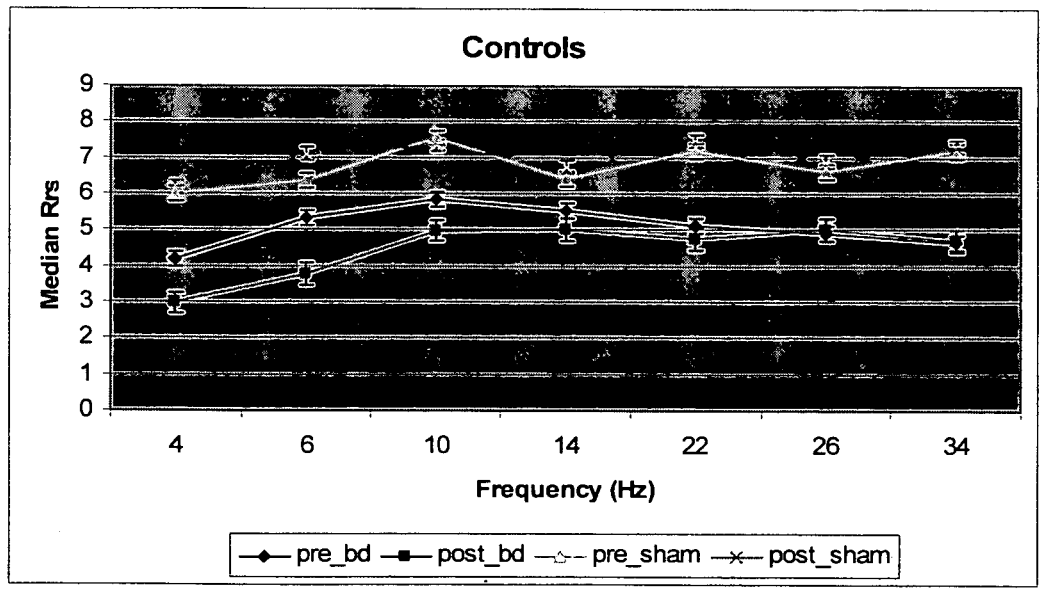
FIG. 9 is a plot of the median Rrs in control children before and after administration of bronchrodilator or sham saline dose.

There was a slight change in median Rrs with bronchodilator administration in control children at low frequencies less than 14 Hz but not at higher frequencies (FIG. 9).

Figure 10:
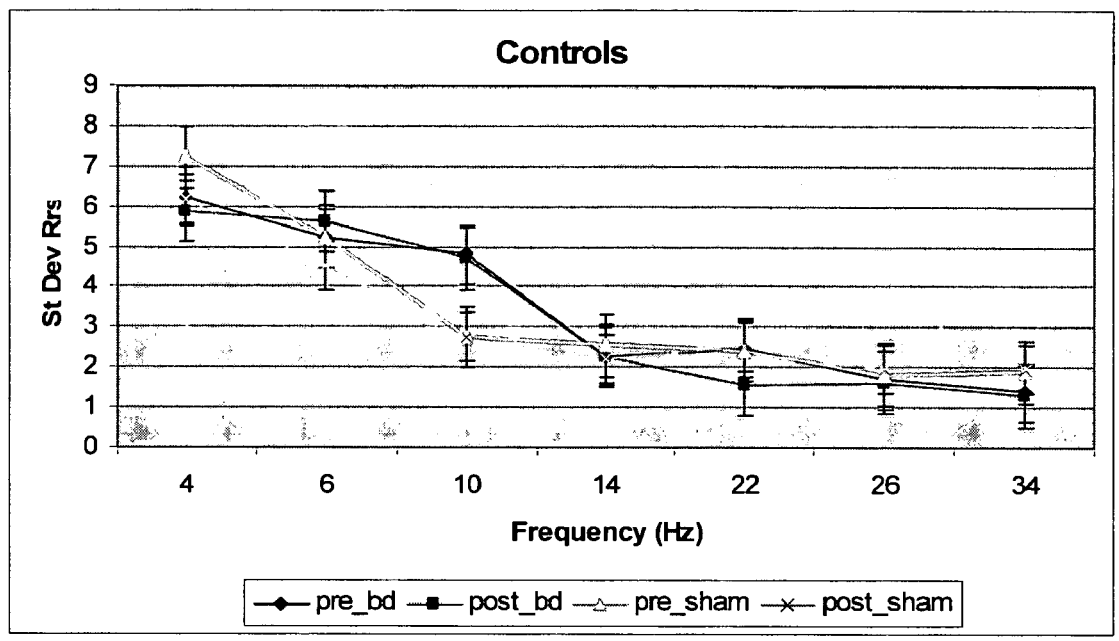
FIG. 10 is a plot of the standard deviation of Rrs in control children vs. frequency before and after administration of a bronchodilator or sham saline dose.

There was no significant change in standard deviation of Rrs with either placebo or bronchodilator administration in control children at any frequency (FIG. 10).

As shown in FIG. 16, there is no significant difference found with BD in control subjects. Thus, a decrease in variation of resistance by FOT at frequencies not affected by breathing noise that occur with a bronchodilator may provide a useful measure of elevated airway smooth muscle activity that occurs in asthma.

Figure 11:
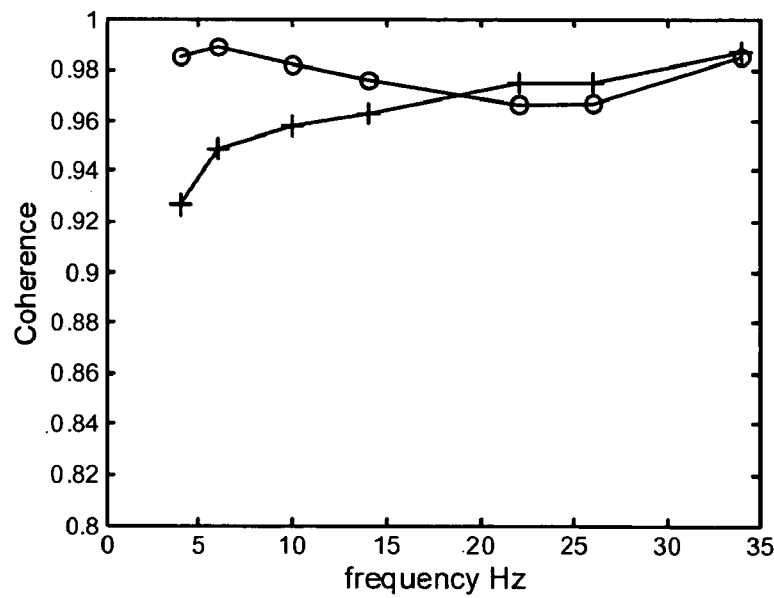
FIG. 11 is a plot of coherence calculated between pressure (circles) and flow (crosses) signals from two different representative subjects at the oscillation frequencies.
Figure 12:
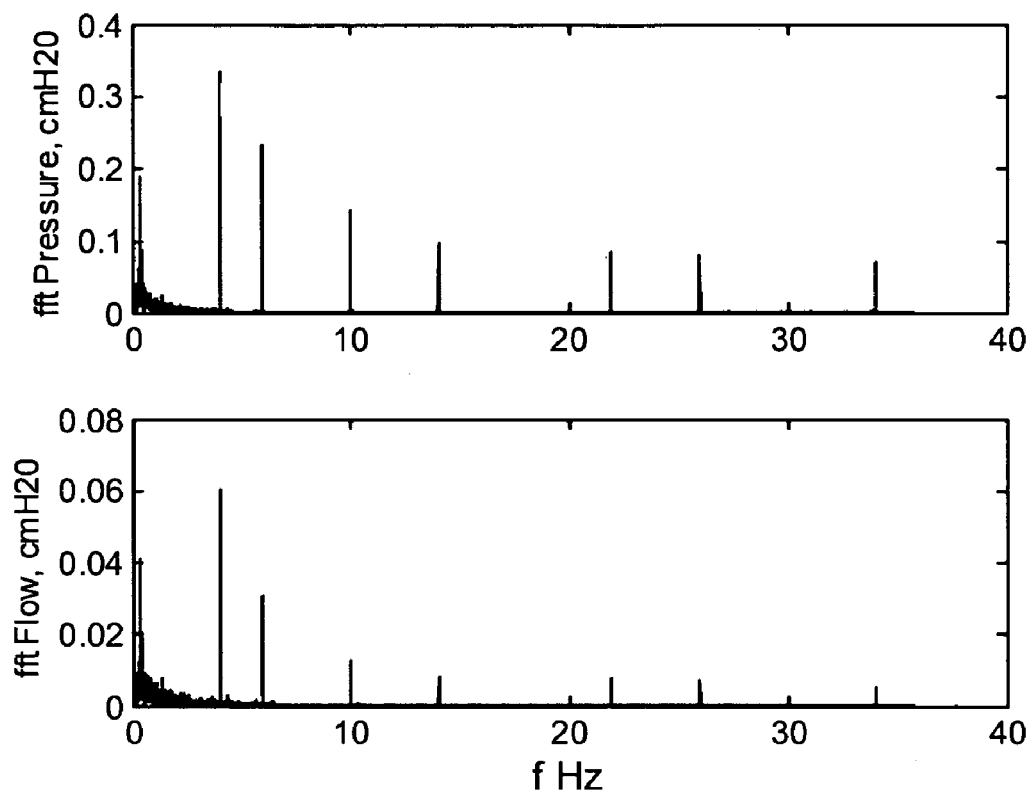
FIG. 12 is a representative example of magnitudes of fast Fourier transformed pressure and flow signals vs. frequency showing the oscillation frequencies used (4, 10, 14, 22, 26, 34 Hz) and breathing noise at low frequencies.
Figure 13:
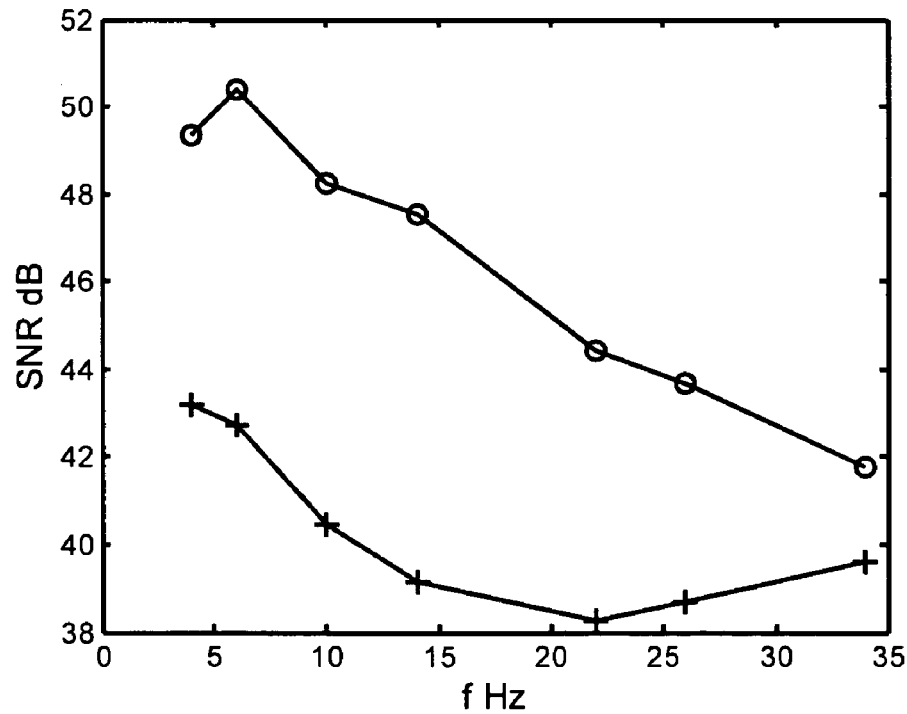
FIG. 13 is a representative plot of signal to noise ratios computed from data in FIG. 12 vs. frequency for pressure signal (circles) and flow signals (squares) for each oscillation frequency.

FIG. 11 is a plot of coherence between pressure (circles) and flow signals (crosses), FIG. 12 is a plot of the Fourier transformed pressure and flow signals and, FIG. 13 is a plot of the signal to noise ratios for pressure (circles) and for flow (crosses) for each oscillation frequency. Signal to noise was calculated in the frequency domain for each oscillation frequency using as a measure of the noise amplitude the noise present in the frequencies adjacent to the oscillation frequencies. Signals were considered to be valid if their coherence was greater than 0.9, and also inferred that the high signal to noise ratios of greater than 20 indicated good signal quality.

Figure 19:
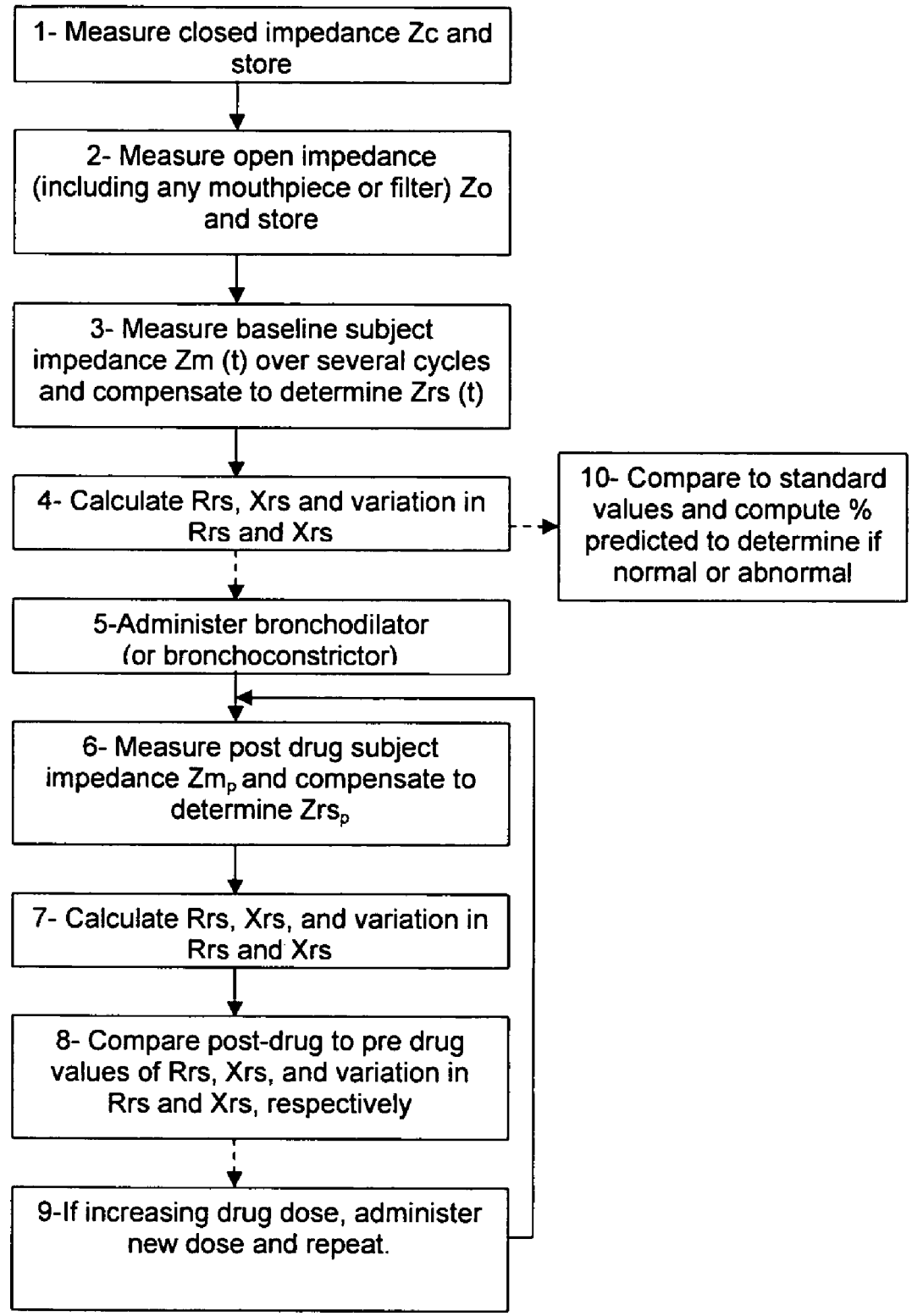
FIG. 19 is a flow chart of a method to determine baseline Rrs, Xrs and SDRs and the changes in these values in response to bronchoactive agents; and, FIG. 20 is a flow chart of a method to determine baseline values of Rrs, Xrs and SDRs, and changes in these values in response to bronchoactive agents.

With reference to FIG. 19, a method is described for determining baseline values of Rrs, Xrs and SDRs and the changes in these values in response to bronchoactive agents. In this embodiment, at step 1, closed impedance Zc is measured and stored. At step 2, open impedance Zo is measured and stored. At step 3, the baseline subject impedance Zm(t) over several cycles is measured and compensated over several cycles to determine Zrs(t). At step 4, Rrs, Xrs and variations in Rrs and Xrs are measured and if desired are compared (step 10) to standard values to compute % predicted to determine if the Rrs, Xrs and variation in Xrs and Rrs are normal or abnormal. At step 5, a bronchoactive agent may be administered to the patient. At step 6, the post drug impedance $Zm_p$ is measured and compensated to determine $Zrs_p$. At step 7, Rrs, Xrs and variation in Rrs and Xrs are calculated. At step 8, post-drug and pre-drug values of Rrs, Xrs and variations in Rrs and Xrs are measured. Optionally, if the drug dose is increased or repeated at step 9, steps 6-8 are repeated.

Figure 20:
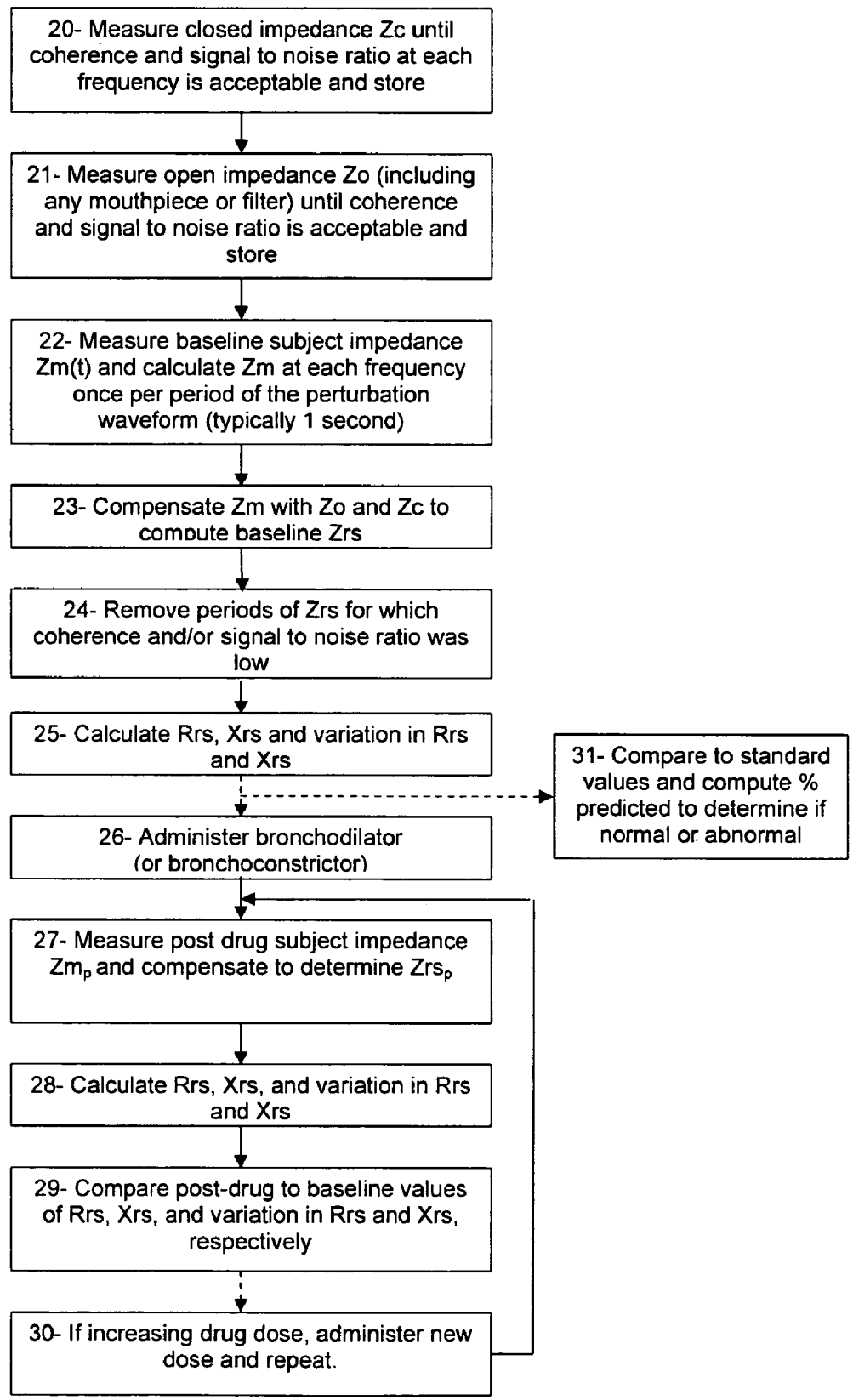

With reference to FIG. 20, an alternate method is described for determining baseline values of Rrs, Xrs and SDRs and the changes in these values in response to bronchoactive agents. In this method at step 20, closed impedance Zc is measured until coherence and signal to noise ratio at each frequency is acceptable and stored. At step 21, open impedance Zo is measured until coherence and signal to noise ratio is acceptable and stored. At step 22, the baseline subject impedance Zm(t) is measure and Zm at each frequency is calculated once per period of the perturbation waveform. At step 23, Zm is compensated with Zo and Zc to compute baseline Zrs. At step 24, periods of Zrs are removed for which coherence and/or signal to noise ratio was low. At step 25, Rrs, Xrs and variation in the Rrs and Xrs are calculated and if desired are compared (step 31) to standard values to compute % predicted to determine if normal or abnormal. At step 26, a bronchoactive agent may be administered. At step 27, post drug impedance $Zm_p$ is measured and compensated to determine $Zrs_p$. At step 28, Rrs, Xrs and variations in Rrs and Xrs are calculated. At step 29, baseline values of Rrs, Xrs and variations in Rrs and Xrs are compared to post-drug values. At step 30, if increasing or repeating the drug dose, the increased drug dose is administered and steps 27-29 are repeated.

[i] http://www.who.int/mediacentre/factsheets/fs206/en/
[ii] http://www.lungusa.org/asthma/ascpedfac99.html
[iii] http://www.getasthmahelp.org/quickfacts.asp
[iv] American Thoracic Society/European Respiratory Society. Respiratory mechanics in infants: physiologic evaluation in health and disease. Am Rev Respir Dis 1993; 147:474-496.
[v] Sly P D, Hayden M J, Petak F, Hantos Z. Measurement of low frequency respiratory impedance in infants. Am J Respir Crit Care Med 1996; 154:161-166.
[vi] Goldman M D. Clinical application of forced oscillation. Pulm Pharm & Therapeutics 2001; 14:341-350.
[vii] Navajas D, Farre R. Forced oscillation technique: from theory to clinical applications. Monaldi Arch Cheat Dis 2001; 56:6,555-562.
[viii] Dubois A, Brody A, Lewis D, and Burgess B. Oscillation mechanics of lungs and chest in man. J Appl Physiol 1956; 8:587-94.
[ix] Ducharme F M, Davis G M, Ducharme G R. Pediatric reference values for respiratory resistance measured by forced oscillation. Chest 1998; 113:1322-1328.
[x] Delacourt C, Lorino H, Herve-Guillot M, Reinert P, Harf A, Housset B. Use of the forced oscillation technique to assess airway obstruction and reversibility in children. Am J Respir Crit Care 2000; 161:730-736.
[xi] Lebecque P, Stanescu D. Respiratory resistance by the forced oscillation technique in asthmatic children and cystic fibrosis patients. Eur Respir J 1997; 10: 891-895.
[xii] Mazurek H K, Marchal F, Derelle J, Hatahet R, Moneret-Vautrin D, Monin P. Specificity and sensitivity of respiratory impedance in assessing reversibility of airway obstruction in children. Chest 1995; 107:996-1002.
[xiii] Delacourt C, Lorino H, Fuhrman C, Herve-Guillot M, Reinert R, Harf A, Housset B. Comparison of the forced oscillation technique and the interrupter technique for assessing airway obstruction and its reversibility in children. Am J Respir Crit Care Med. 2001 Sep. 15; 164(6): 965-72.
[xiv] Hellinckx J, De Boeck K, Demedts M. No paradoxical bronchodilator response with forced oscillation in children with cystic fibrosis. Chest 1998; 113(1):55-59.
[xv] Van Noord J A, Clement J, Van de Woestijne K P, Demedts M. Total respiratory resistance and reactance in patients with asthma, chronic bronchitis and emphysema. Am Rev Respir Dis 1991; 143:922-927.
[xvi] Zerah F, Lorino A-M, Lorino H, Harf A, Macquin-Mavier I. Forced oscillation technique vs. spirometry to assess bronchodilation in patients with asthma and COPD. Chest 1995; 108:41-47.
[xvii] Farre R, Peslin R, Rotger M, Barbera J A, Navajas D. Forced oscillation total respiratory resistance and spontaneous breathing lung resistance in COPD patients. Eur Respir J 1999; 14:172-178.
[xviii] King T E Jr. A new look at the pathophysiology of asthma. J Natl Med Assoc 1999; 91(8):9S-15S.
[xix] O'Byrne P M, Inman M D. New considerations about measuring airway hyperresponsiveness. J Asthma 2000; 37(4):293-302.
[xx] Brusasco V, Crimi E, Barisione C, Spanevello A, Rodarte J R, Pellegrino R. Airway responsiveness to methacholine: effects of deep inhalations and airway inflammation. J Appl Physiol 1999; 87:567-573.
[xxi] Que C L, Kenyon C M, Olivenstein R, Maklem P T, Maksym G N. Homeokinesis and short-term variability of human airway caliber. J Appl Physiol 2001; 91:1131-1141.
[xxii] Cauberghs M, Van de Woestijine K. Changes of respiratory input impedance during breathing in humans. J Appl Physiol 1992; 73:2355-2362.
[xxiii] Nadel J A, Tierney D F. Effect of a previous deep inspiration on airway resistance in man. J Appl Physiol 1961; 16:717-719.
[xxiv] Skloot G, Permutt S, Togias A. Airway hyperresponsiveness in asthma: a problem of limited smooth muscle relaxation with inspiration. J Clin Invest 1995; 96:2393-2403.
[xxv] Kapsali T, Permutt S, Laube B, Scichilone N, Togias A. Potent bronchoprotective effect of deep inspiration and its absence in asthma. Am Rev Resp Dis 1987; 135:591-596.

The invention claimed is:

1. A method of assessment of airway variability in airway responsiveness or asthma comprising the steps of:
   a) measuring airway resistance by a forced oscillation technique utilizing a pressure signal and a flow signal at each of a plurality of input frequencies during a plurality of respiratory cycles of a patient;
   b) collecting and processing airway resistance data measured in step a) using a data acquisition system;
   c) calculating a standard deviation of the airway resistance for the patient with the airway resistance data from step b) using a computer; and
   d) correlating the standard deviation of the airway resistance from step c) of the patient to a standard curve obtained from a population of asthmatics and non-asthmatics to quantify a degree of asthma of the patient.

2. A method as in claim 1 further comprising the steps of determining a noise level and a signal to noise ratio contributing to airway resistance for each input frequency, including:
   obtaining the pressure signal and the flow signal;
   obtaining a coherence of the pressure signal and flow signals;
   obtaining a Fourier transform of multiple cycles of pressure and a Fourier transform of multiple cycles of flow;

obtaining an absolute value of the pressure and flow signals at each input frequency;

obtaining an average of the absolute values of the pressure and flow signals for a region of frequencies adjacent to input frequencies not including any input frequencies that the signal to noise ratio for either pressure or flow is a ratio of the signal, determined as a magnitude of the pressure or flow at the input frequency, divided by the noise level, determined as a magnitude of the pressure or flow in a region of frequencies adjacent to the input frequency not including any input frequency.

3. A method as in claim 1 wherein the airway resistance of a patient is measured over 1 minute using pressure oscillations having input frequencies ranging from 4 Hz to 34 Hz.

4. A method as in claim 1 wherein the airway resistance of a patient is measured over 1 minute using pressure oscillations having input frequencies ranging from 10 Hz to 34 Hz.

5. A method of determining a pharmacological agonist or antagonist's effectiveness on altering airway diameter variability comprising the steps of:
   a) measuring a patient's airway resistance by a forced oscillation technique utilizing a plurality of input frequencies during a plurality of respiratory cycles;
   b) measuring the patient's airway resistance by the forced oscillation technique utilizing the plurality of input frequencies of step a) during a plurality of respiratory cycles of the patient having been administered a pharmacological agonist or antagonist;
   c) collecting and processing airway resistance data measured in steps a) and b) using a data acquisition system;
   d) calculating a standard deviation of the airway resistance for the patient for each of steps a) and b) using a computer; and,
   e) comparing the standard deviation of the airway resistance to determine the effectiveness of the pharmacological agonist or antagonist.

6. A method as in claim 3 wherein the pharmacological agonist or antagonist is a bronchodilator.

7. A method as in claim 5 wherein the pharmacological agonist or antagonist is a bronchoconstrictor.

8. A method of determining a pharmacological agonist or antagonist's effectiveness on altering airway diameter variability comprising the steps of:
   a) measuring airway reactance (Xrs) by a forced oscillation technique using a forced oscillation measuring device in a patient prior to administration of a pharmacological agonist or antagonist utilizing a plurality of input frequencies during a plurality of respiratory cycles;
   b) measuring airway reactance (Xrs) by a forced oscillation technique using the measuring device in the patient post administration of the pharmacological agonist or antagonist utilizing the plurality of input frequencies of step a) during a plurality of respiratory cycles;
   c) collecting and processing airway reactance data measured in steps a) and b) using a data acquisition system;
   d) calculating a standard deviation of the airway reactance data from step c) for the patient for each of the pre- and post-administration airway reactance data using a computer; and,
   e) comparing the standard deviation of the pre- and post-administration airway reactance data to determine the effectiveness of the pharmacological agonist or antagonist.

9. A method as in claim 8 wherein the pharmacological agonist or antagonist is a bronchodilator.

10. A method as in claim 8 wherein the pharmacological agonist or antagonist is a bronchoconstrictor.

11. A method as in claim 8 where impedance of the measuring device is removed by a compensation algorithm.

12. A method for determining baseline values of resistance, reactance and standard deviation of resistance and the changes in these values in response to bronchoactive agents comprising the steps of:
   a, measuring and storing closed impedance (Zc) in a data acquisition system;
   b. measuring and storing open impedance (Zo) in a data acquisition system;
   c. measuring and compensating baseline subject impedance Zm(t) over several cycles to determine a subject's respiratory impedance (Zrs(t));
   d. measuring and comparing resistance and reactance and variations in resistance and reactance;
   e. administering a bronchoactive agent to a patient;
   f. measuring post-drug impedance $Zm_p$ and compensating to determine a subject's post-drug respiratory impedance $Zrs_p$;
   g. calculating post-drug and pre-drug resistance and reactance and variation in resistance and reactance using a computer;
   h. comparing post-drug and pre-drug values of resistance and reactance and variations in resistance and reactance to standard values to determine if the resistance and reactance and variation in resistance and reactance are normal or abnormal.

13. A method of assessment of airway variability in airway responsiveness or asthma comprising the steps of:
   a) measuring airway resistance by a forced oscillation technique utilizing either a single or a plurality of input frequencies during a plurality of respiratory cycles of a patient over a number of sampling periods to obtain airway resistance data sufficient to quantify a standard deviation of any underlying airway resistance of the patient;
   b) collecting and processing airway resistance data measured in step a) using a data acquisition system;
   c) calculating the standard deviation of airway resistance for the patient with the airway resistance data from step b) using a computer; and,
   d) correlating the standard deviation of the airway resistance from step c) of the patient to a standard curve obtained from a population of asthmatics or non-asthmatics to quantify a degree of asthma of the patient.

14. A method of assessment of airway variability in airway responsiveness or asthma comprising the steps of:
   a) measuring airway resistance by a forced oscillation technique utilizing either a single or a plurality of input frequencies during a plurality of respiratory cycles of a patient over a number of sampling periods to obtain airway resistance data sufficient to statistically quantify a standard deviation underlying differences in airway resistance of the patient between sampling periods;
   b) collecting and processing the airway resistance data measured in step a) using a data acquisition system;
   c) calculating the standard deviation of the airway resistance for the patient with the airway resistance data from step b) using a computer; and,
   d) correlating the standard deviation of the airway resistance from step c) of the patient to a standard curve obtained from a population of asthmatics and non-asthmatics to quantify a degree of asthma of the patient.

15. A method of determining a pharmacological agonist or antagonist's effectiveness on altering airway diameter variability comprising the steps of:

a) measuring a patient's airway resistance by a forced oscillation technique utilizing a plurality of input frequencies during a plurality of respiratory cycles of the patient over a number of sampling periods to obtain airway resistance data sufficient to statistically quantify a standard deviation underlying differences in airway resistance of the patient between sampling periods;

b) measuring the patient's airway resistance by a forced oscillation technique utilizing the plurality of input frequencies of step a) during a plurality of respiratory cycles of the patient having been administered a pharmacological agonist or antagonist over a number of sampling periods to obtain airway resistance data sufficient to statistically quantify a standard deviation underlying differences in airway resistance of the patient between sampling periods;

c) collecting and processing the patient's airway resistance data measured in steps a) and b) using a data acquisition system;

d) calculating the standard deviation of the patient's airway resistance for each of steps a) and b) using a computer; and, e) comparing the standard deviation of the patient's airway resistance to determine the effectiveness of the pharmacological agonist or antagonist.

16. A method of determining a pharmacological agonist or antagonist's effectiveness on altering airway diameter variability comprising the steps of:

a) measuring a patient's airway reactance (Xrs) by a forced oscillation technique utilizing a plurality of input frequencies during a plurality of respiratory cycles of the patient over a number of sampling periods prior to administration of the pharmacological agonist or antagonist;

b) measuring the patient's airway reactance (Xrs) by a forced oscillation technique utilizing the plurality of input frequencies of step a) during a plurality of respiratory cycles over a number of sampling periods after administration of the pharmacological agonist or antagonist to obtain pre- and post-administration airway reactance data sufficient to statistically quantify a standard deviation underlying differences in the patient's airway reactance between sampling periods;

c) collecting and processing the pre and post-administration airway reactance data measured in step a) using a data acquisition system;

d) calculating the standard deviation of the airway reactance data from step a) for the patient for each of the pre- and post-administration airway reactance data using a computer; and, e) comparing the standard deviation of the pre- and post-administration airway reactance data to determine the effectiveness of the pharmacological agonist or antagonist.

17. A method of assessment of airway variability in airway responsiveness or asthma comprising the steps of a) measuring airway resistance by a forced oscillation technique utilizing a plurality of input frequencies during a plurality of respiratory cycles of a patient;

b) collecting and processing airway resistance data measured in step a) using a computer;

c) calculating a standard deviation of the airway resistance for the patient with the airway resistance data from step b) using a computer; and d) correlating the standard deviation of the airway resistance from step c) of the patient to a standard curve obtained from a population of asthmatics and non-asthmatics to quantify a degree of asthma of the patient.

18. A method of determining a pharmacological agonist or antagonist's effectiveness on altering airway diameter variability comprising the steps of:

a) measuring a patient's airway resistance by a forced oscillation technique utilizing a plurality of input frequencies during a plurality of respiratory cycles;

b) measuring the patient's airway resistance by a forced oscillation technique utilizing the plurality of input frequencies from step a) during a plurality of respiratory cycles having been administered a pharmacological agonist or antagonist;

c) collecting and processing airway resistance data measured in steps a) and b) using a computer;

d) calculating a standard deviation of the patient's airway resistance for each of steps a) and b) using a computer; and e) comparing the standard deviation of the patient's airway resistance pre- and post-administration of the pharmacological agonist or antagonist to determine the pharmacological agonist or antagonist's effectiveness on altering airway diameter variability.

19. A method as in claim 18 wherein the pharmacological agonist or antagonist is a bronchodilator.

20. A method as in claim 18 wherein the pharmacological agonist or antagonist is a bronchoconstrictor.

21. A method of determining a pharmacological agonist or antagonist's effectiveness on altering airway diameter variability comprising the steps of:

a) measuring a patient's airway reactance (Xrs) prior to administration of a pharmacological agonist or antagonist by a forced oscillation technique utilizing a plurality of input frequencies during a plurality of respiratory cycles;

b) measuring the patient's airway reactance (Xrs) post administration of the pharmacological agonist or antagonist by the forced oscillation technique utilizing the plurality of input frequencies of step a) during a plurality of respiratory cycles;

c) collecting and processing airway reactance data measured pre- and post-administration of a pharmacological agonist or antagonist in step a) using a computer;

d) calculating a standard deviation of the airway reactance data from step b) for the patient for each of the pre- and post-administration airway reactance data using a computer; and e) comparing the standard deviation of the pre- and post-administration airway reactance data to determine the pharmacological agonist or antagonist's effectiveness on altering airway diameter variability.

22. A method as in claim 21 wherein the pharmacological agonist or antagonist is a bronchodilator.

23. A method as in claim 21 wherein the pharmacological agonist or antagonist is a bronchoconstrictor.

24. A method as in claim 21 further comprising removing impedance of a measuring device by a compensation algorithm.

25. A method for assessment of airway variability in airway responsiveness or asthma comprising:

a) providing a forced oscillation generating device, said oscillation generating device comprising a low-amplitude pressure generator;

b) measuring airway resistance by a forced oscillation technique utilizing pressure oscillations having a plurality of input frequencies generated by said forced oscillation generating device during a plurality of respiratory cycles of a patient;

c) collecting and processing airway resistance data using a data acquisition system;

d) calculating a standard deviation of the airway resistance for the patient using the airway resistance data from step c); and e) correlating the standard deviation of the airway resistance from step d) of the patient to a standard curve obtained from a population of at least one of asthmatics and non-asthmatics to quantify a degree of asthma of the patient.

26. The method as in claim 25, wherein the plurality of input frequencies range from 4 Hz to 34 Hz.

27. The method as in claim 25, wherein the airway resistance of the patient is measured over 1 minute using pressure oscillations having input frequencies ranging from 10 Hz to 34 Hz.

* * * * *

UNITED STATES PATENT AND TRADEMARK OFFICE
CERTIFICATE OF CORRECTION

PATENT NO. : 8,172,765 B2
APPLICATION NO. : 11/121031
DATED : May 8, 2012
INVENTOR(S) : Geoffrey N. Maksym et al.

Page 1 of 1

It is certified that error appears in the above-identified patent and that said Letters Patent is hereby corrected as shown below:

Column 11, claim number 6, line number 37, which reads "A method as in claim 3" should read "A method as in claim 5".

Signed and Sealed this
Twenty-ninth Day of January, 2013

David J. Kappos
*Director of the United States Patent and Trademark Office*